United States Patent [19]

Duffett

[11] Patent Number: Plant 6,124

[45] Date of Patent: Mar. 8, 1988

[54] CHRYSANTHEMUM PLANT NAMED OMEGON

[75] Inventor: William E. Duffett, Salinas, Calif.

[73] Assignee: Yoder Brothers, Inc., Barberton, Ohio

[21] Appl. No.: 833,081

[22] Filed: Feb. 26, 1986

[51] Int. Cl.[4] ..... A01H 5/00

[52] U.S. Cl. ..... Plt./77

[58] Field of Search ..... Plt./77

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Omegon particularly characterized by its incurved capitulum form; standard capitulum type; white ray floret color; diameter across face of capitulum of 125 to 150 mm. at maturity; uniform nine week photoperiodic flowering response to short days; medium plant height when grown single stem; and 13° C. minimum temperature tolerance for initiation and development of flowering buds.

3 Drawing Sheets

The present invention comprises a new and distinct cultivar of Chrysanthemum, botanically known as *Dentrenthema morifolium,* Ramat., previously *Chrysanthemum morifolium,* Ramat., and referred to by the cultivar name Omegon.

Omegon, identified as 79R57002, was originated from a cross made by me in a controlled breeding program in Salinas, Calif., in 1979. The female parent of Omegon, identified as 79*02014, was an unnamed seedling. The male parent of Omegon was the cultivar identified as Aspen, disclosed in U.S. Plant Pat. No. 5,240.

Omegon was discovered and selected as one flowering plant within the progeny of the stated cross by William E. Duffett in September of 1980, in a controlled environment in Salinas, Calif.

The first act of asexual reproduction of Omegon was accomplished when vegetative cuttings were taken from the initial selection in December of 1980 in a controlled environment in Salinas, Calif. by technicians working under formulations established and supervised by William E. Duffett.

Horticultural examination of controlled flowerings of successive plantings has shown that the unique combination of characteristics as herein disclosed for Omegon are firmly fixed and are retained through successive generations of asexual reproduction.

Omegon has not been observed under all possible environmental conditions. The phenotype may vary significantly with variations in environment such as temperature, light intensity and day length.

The following observations, measurements and comparisons describe plants grown in Salinas, Calif. and Bogota, Colombia under greenhouse conditions which approximate those generally used in commercial greenhouse practice.

The following traits have been repeatedly observed and are determined to be basic characteristics of Omegon which, in combination, distinguish this Chrysanthemum as a new and distinct cultivar:

1. Incurved capitulum form.
2. Standard capitulum type.
3. White ray floret color.
4. Diameter across face of capitulum from 125 to 150 mm. at maturity.
5. Uniform nine week photoperiodic flowering response to short days.

6. Medium plant height, requiring two to three long day weeks prior to short days to attain a flowered plant height of 100 to 110 cm. for year around flowerings.
7. Low temperature tolerance of 13° C. for initiation and development when grown in single stem cut standard programs with a continuous dark period of 12 to 13 hours.

The accompanying photographic drawings show typical inflorescence and leaf characteristics of Omegon, with the colors being as nearly true as possible with illustrations of this type.

Sheet 1 is a color photograph of Omegon grown as a single stem cut standard.

Sheet 2 is a black and white photograph of three views of the inflorescence of Omegon.

Sheet 3 is a black and white photograph showing the upper and under sides of the leaves of Omegon at three stages of development (mature, intermediate and immature).

Of the commercial cultivars known to the inventor, the most similar in comparison to Omegon is Albatross, an unpatented cultivar. Reference is made to attached Chart A, which compares certain characteristics of Omegon to the same characteristics of Albatross, when grown in Bogota, Colombia. Similar traits are capitulum form and type, color and plant height. Omegon has a larger flower, faster flowering response, and superior tolerance of low temperatures for bud initiation and development.

In the following description, color references are made to The Royal Horticultural Society Colour Chart. The color values were determined on plant material grown in Salinas, Calif. on Nov. 14, 1985.

Classification:

*Botanical.*—*Dentrenthema morifolium,* Ramat., cv Omegon.

*Commercial.*—Incurved standard cut mum.

INFLORESCENCE

A. Capitulum:

*Form.*—Incurved.

*Type.*—Standard.

*Diameter across face.*—125 to 150 mm. at maturity.

B. Corolla of ray florets:

*Color (general tonality from a distance of three meters)*:—White.

*Color (upper surface)*.—155D to 158D.

*Color (under surface)*.—155D.

*Shape*.—Oblong.

C. Corolla of disc florets:

*Color (mature)*.—4B.

*Color (immature)*.—150A.

D. Reproductive organs:

*Androecium*.—Present disc florets only, very few, scant pollen.

*Gynoecium*.—Present both ray and disc florets.

PLANT

A. General appearance:

*Height*.—Medium; 100 to 110 cm. as a flowering plant from a rooted cutting with two to three long day weeks for year around flowerings maintaining a continuous dark period of 12 to 13 hours.

B. Foliage:

*Color (upper surface)*.—147A.

*Color (under surface)*.—147B.

*Shape*.—Deeply lobed, slightly serrated.

CHART A

COMPARISON OF OMEGON AND ALBATROSS

DIAMETER

CHART A-continued

COMPARISON OF OMEGON AND ALBATROSS

| CULTIVAR | RAY FLORET COLOR | CAPITULUM FORM AND TYPE | ACROSS FACE OF CAPITULUM |
|---|---|---|---|
| OMEGON | WHITE | INCURVED STANDARD | 125 to 150 mm. |
| ALBATROSS | WHITE | INCURVED STANDARD | 115 to 125 mm. |

| CULTIVAR | PLANT HEIGHT | FLOWERING RESPONSE PERIOD | TOLERANCE OF 13° C. |
|---|---|---|---|
| OMEGON | MEDIUM | NINE WEEKS | GOOD |
| ALBATROSS | MEDIUM | TEN TO ELEVEN WEEKS | MARGINAL |

COMPARISONS MADE OF PLANTS GROWN AS SINGLE STEM STANDARD CUT MUMS IN BOGOTA, COLOMBIA

I claim:

1. A new and distinct Chrysanthemum plant named Omegon, as described and illustrated, and particularly characterized as to uniqueness by the combined characteristics of incurved capitulum form; standard capitulum type; white ray floret color; diameter across face of capitulum of 125 to 150 mm. at maturity; uniform nine week photoperiodic flowering response to short days; medium plant height when grown single stem; and 13° C. minimum temperature tolerance for initiation and development of flowering buds.

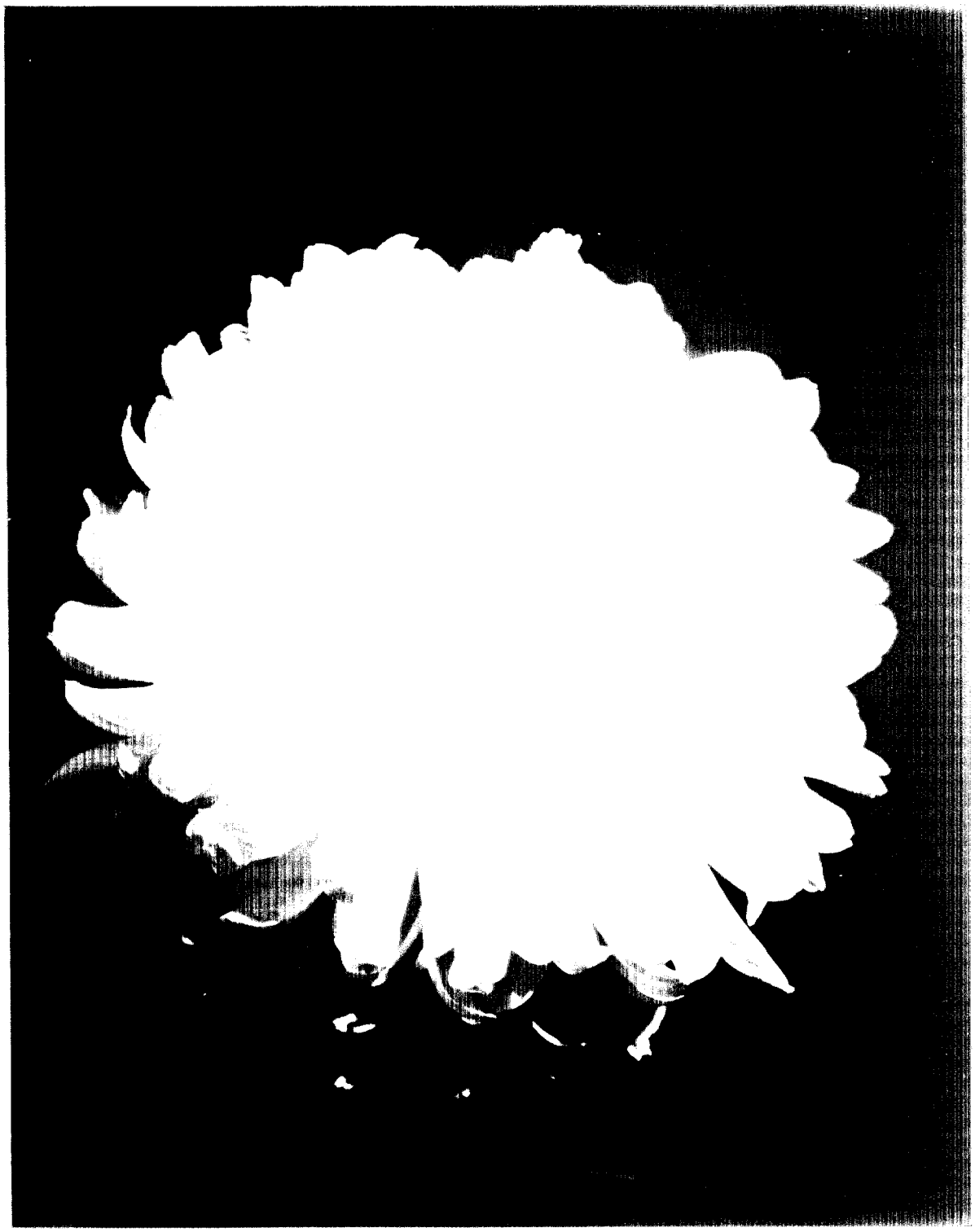

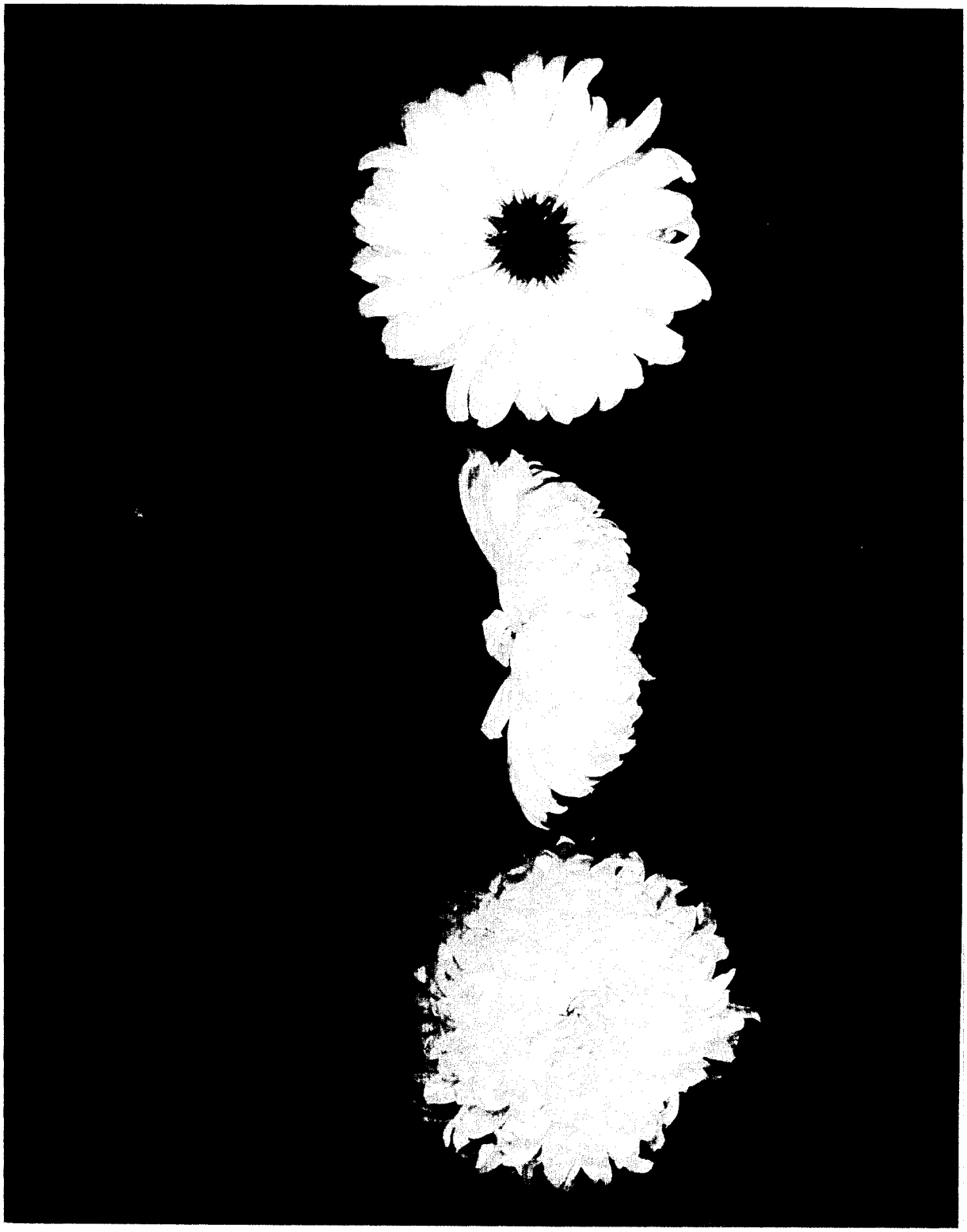

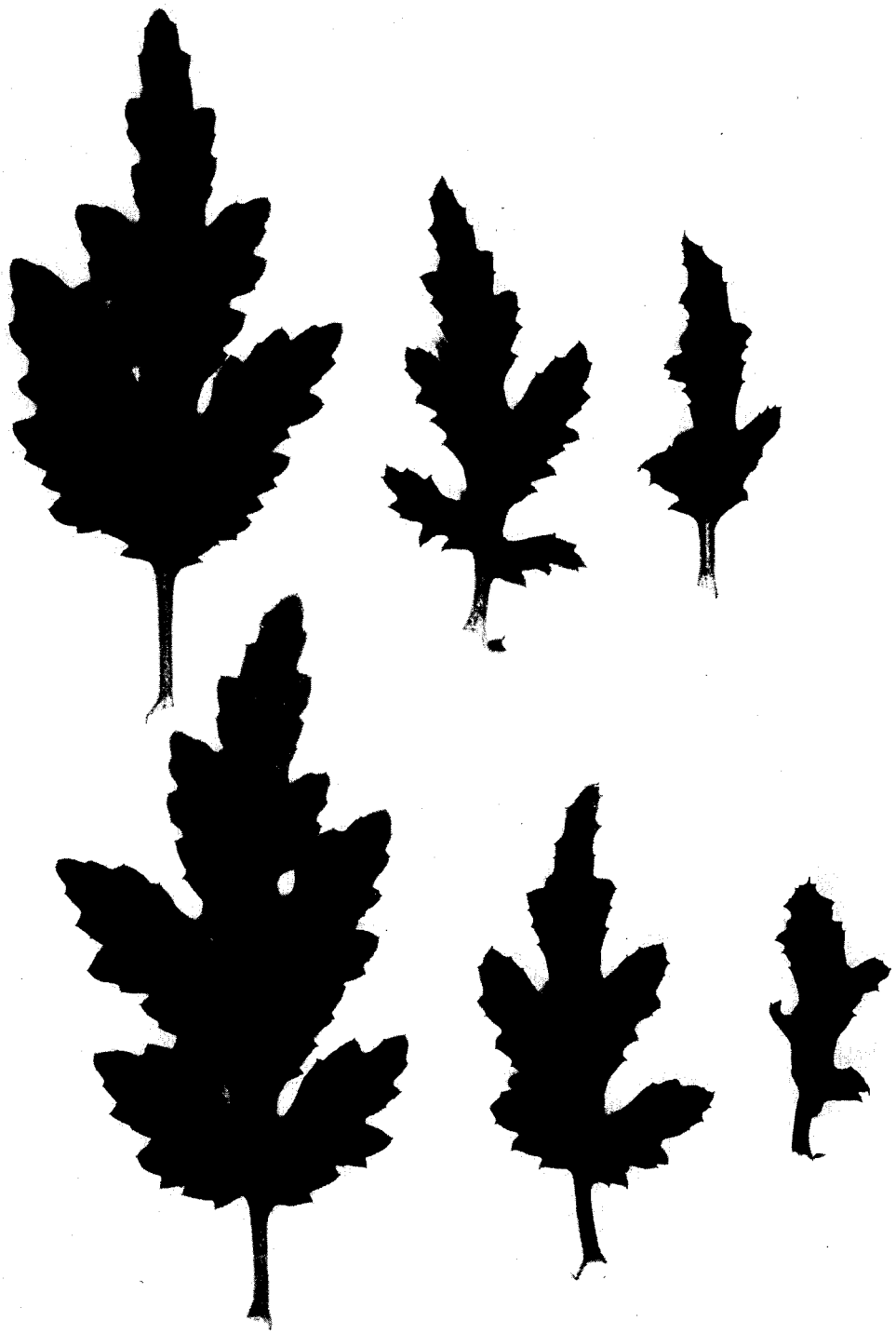

* * * * *